United States Patent [19]

Law

[11] Patent Number: 5,754,296
[45] Date of Patent: May 19, 1998

[54] ELLIPSOMETRIC MICROSCOPE

[75] Inventor: Bruce M. Law, Manhattan, Kans.

[73] Assignee: Kansas State University Research Foundation, Manhattan, Kans.

[21] Appl. No.: 759,080

[22] Filed: Nov. 27, 1996

Related U.S. Application Data

[63] Continuation of Ser. No. 407,466, Mar. 20, 1995, abandoned.

[51] Int. Cl.$^6$ .............................. G01J 4/00; G01B 11/06
[52] U.S. Cl. .................................. 356/369; 356/382
[58] Field of Search ............................ 356/364–370, 356/381, 382

[56] References Cited

U.S. PATENT DOCUMENTS

| | | | |
|---|---|---|---|
| 3,992,104 | 11/1976 | Watanabe | 356/369 |
| 4,306,809 | 12/1981 | Azzam | 356/369 |
| 4,516,855 | 5/1985 | Korth . | |
| 4,523,848 | 6/1985 | Gorman et al. | 356/369 |
| 4,999,014 | 3/1991 | Gold et al. | 356/369 |
| 5,076,696 | 12/1991 | Cohn et al. . | |
| 5,432,607 | 7/1995 | Taubenblatt | 356/369 |
| 5,450,205 | 9/1995 | Sawin et al. | 356/382 |

OTHER PUBLICATIONS

Liu et al.; Image Scanning Ellipsometry for Measuring Nonuniform Film Thickness Profiles; Applied Optics, vol. 33, No. 7, pp. 1223–1229 (Mar. 1, 1994).

Henon et al.; Microscope at the Brewster Angle: Direct Observation of First–Order Phase Transitions in Monolayers; Rev. Sci. Insrum. 62(4), Apr. 1991, pp. 936–939.

Beaglehole; Performance of a Microscopic Imaging Ellipsometer, Rev. Sci. Instrum. 59(12), Dec., 1988, pp. 2557–2559.

Cohn et al.; Dynamic Imaging Microellipsometry: Theory, System, Design and Feasibility Demonstration; Applied Optics, vol. 27, No. 22, Nov. 15, 1988, pp. 4664–4671.

*Primary Examiner*—Hoa Q. Pham
*Attorney, Agent, or Firm*—Hovey, Williams, Timmons & Collins

[57] ABSTRACT

The ellipsometric microscope (10) broadly includes a light source (14) for emitting a beam of monocromatic, collimated light, an adjustable support assembly (12) for directing the light beam along an incident path (56) for impingement on a film sample (58) at a predetermined angle for reflectance off of the sample along a reflectance path (60), and a detector (34) for detecting the reflectance beam. A polarizer (20) is positioned along the incident path (56) for elliptically polarizing the incident beam, and a remotely controllable variable retarder (22) is also positioned along the incident path (56) for altering the elliptical polarization of the incident beam. A beam expander (30) is positioned along the reflectance path (60) between the film sample (58) and the detector (34) for expanding the beam of light, and permitting only passage of parallel components of the reflectance beam. An analyzer (36) is coupled with the detector (34) for analyzing the reflectance beam for determining the thickness of the film sample (58).

13 Claims, 1 Drawing Sheet

5,754,296

ELLIPSOMETRIC MICROSCOPE

This is a continuation of application Ser. No. 08/407,466, filed Mar. 20, 1995 now abandoned.

BACKGROUND OF THE INVENTION

1. Field of the Invention

The present invention relates to devices used to measure the thickness of thin films. More particularly, the invention concerns an ellipsometric microscope having high spatial resolution and thickness sensitivity.

2. Description of the Prior Art

Many situations require the measurement of thin films. Thin films are those films which have a thickness that is much less than the wavelength of visible light. Thin films may include such items as optical coatings, glass coatings, metal coatings, paints, lubricants, and plant nutrition or treatments. Semiconductors and High Tc Superconductors commonly have thin film surfaces as well. In many industries, the need for accurate measurements of thin film thicknesses is critical.

Various devices are known for measuring the thickness of films, such as interferometers, reflectometers, ellipsometrics and ellipsometric microscopes. In broad terms, each of these devices directs an incident beam of electromagnetic energy to the film sample surface for reflection onto a detector. The reflectance beam is then analyzed to determine the thickness of the film. These devices may operate in the visible spectrum, where the wavelength ranges between about $7 \times 10^{-7}$ m and $4 \times 10^{-7}$ m. Reflectometers may additionally operate in the X-ray spectrum, where the wavelength ranges between about $\times 10^{-8}$ m and $\times 10^{-12}$ m.

Visible wavelength interferometers and reflectometers, however, are unable to satisfactorily measure the thickness of thin films. For example, these devices may only be used where the thickness of the film being measured is at least equivalent to the wavelength, $\lambda$, of the incident beam of light. Therefore, visible wavelength interferometers and reflectometers may not be used to measure the thickness of thin films.

Although X-ray reflectometers may be used to measure the thickness of thin films, they have poor lateral spatial resolution. Therefore, while X-ray reflectometers are able to detect an average thickness for an area of the thin film sample, they are unable to accurately yield the thickness of the film sample as a function of the surface position. X-ray reflectometers also present safety concerns which are not present in interferometry, ellipsometry and ellipsometric microscopy. In addition, they are relatively expensive, and generally located at only a few facilities.

In conventional ellipsometry, a beam of polarized light is reflected off of a thin film sample surface, and onto a detector. The elliptically polarized reflectance beam is analyzed to determine the coefficient of ellipticity, $\bar{\rho}$, which may be interpreted in terms of the thickness of the film sample, as will be discussed more fully below.

The elliptically polarized light is the sum of two components, one in the plane of incidence of the light, hereinafter known as the p polarization direction, the other perpendicular to this plane, hereinafter known as the s polarization direction. Upon reflection, the amplitude and phase of the p and s polarization components are altered due to the structure of the surface. These changes are typically represented by the complex reflection amplitudes $r_p = \rho_p e^{i\delta(p)}$ and $r_s = \rho_s e^{i\delta(s)}$ for the p and s polarizations, respectively, where $\rho$ is the absolute amplitude and $\delta$ is the phase. Ellipsometry measures the ratio of these two coefficients, $r_p/r_s$. The greatest sensitivity for an ellipsometric microscope occurs when the incident beam of light is at the Brewster angle, $\theta_B$.

Ellipsometric microscopes broadly include a light source which emits an incident beam of light directed towards the thin film sample, and a detector which is positioned along the reflectance path of the reflectance beam. Ellipsometric microscopes are generally categorized in two families, the PCSA family, and the PSCA family. The PCSA family include, in addition to the light source and detector, a polarizer, a compensator, and an analyzer. The polarizer and compensator are positioned along the incident beam path, and the analyzer is positioned along the reflectance beam path. The polarizer is oriented at a 45° angle with respect to the p and s polarization directions for passage of equal amplitudes in the p and s directions. The compensator, commonly a ¼-wave plate, elliptically polarizes the incidence beam. Ellipsometric microscopes may also be of the PSCA family where the compensator and analyzer are positioned along the reflectance path.

In commercial applications, the detector is commonly a photomultiplier, or a photodiode. The Phase-Modulated Spectroscopic Ellipsometer manufactured by Jobin Yvon/Spex is an example of a conventional ellipsometer. This device may be used to measure the thickness of thin films. Photomultipliers and photodiodes, however, are only able to measure the average film sample thickness along the cross section of the light beam, and thus offer poor lateral spatial resolution.

Ellipsometric microscopes provide excellent thickness sensitivity and higher lateral spatial resolution than X-ray reflectometers or conventional ellipsometers. Recently several research groups have developed ellipsometric microscopes which utilize a charged coupled device (CCD) camera as a detector. CCD cameras typically consist of a large array, such as 512×512, of photosensitive pixels. The pixel to pixel intensity variance detected by the CCD camera provides information about the spatial variation of the thin film thickness.

The image scanning ellipsometer (ISE) developed by Liu, Wayner and Plawsky is a PCSA-type ellipsometric microscope having a CCD camera detector. Their device is based upon null ellipsometry, where the compensator and analyzer are rotated to cause extinction of the beam of polarized light. Once the extinction point, also known as the null point, has been reached, the values of the measured azimuths of the polarizer, analyzer, and compensator are recorded. The coefficient of ellipticity, $\bar{\rho}$, may be determined from these measurements.

The ISE provides excellent thickness sensitivity, however, it only provides thickness information at points where the intensity is null. Therefore, film thickness may not be determined as a continuous function of position, and may only be determined at discrete positions.

The dynamic imaging microellipsometer (DIM) developed by Cohn, Wagner and Kruger is a PSCA-type ellipsometric microscope which operates at a non-Brewster angle. By operating at a non-Brewster angle, this device does not utilize the greater thickness measuring sensitivity of ellipsometric microscopes operating at the Brewster angle.

The DIM utilizes an imaging lens which forms a real image on the CCD camera detector. In using such a lens only one strip of the film sample will be in focus on the camera because different parts of the film sample will be in focus while other parts will be out of focus. This defocusing effect causes an image plane distortion, which may only be overcome by taking and splicing together multiple sets of pictures of the film sample surface representing different positions of the imaging lens in order to create a map of the entire film sample surface where all sections are in focus. Mapping, however, is inherently difficult and often leads to overlapping of adjacent pictures which yields a distorted view of the film sample surface. Defocusing is a serious problem with respect to the use of CCD cameras, and, therefore, to the utility of ellipsometric microscopes.

In order to determine the coefficient of ellipticity, the DIM mechanically rotates the analyzer to four different settings, 0°, 45°, −45°, and 90°, and measures the reflected intensity at each of these settings. These optical instruments, such as analyzers, include unique defects which may only be determined by complex calibration procedures. As a result, rotation of the optical components causes the path of the reflectance beam corresponding to a common position on the film sample surface to be altered with respect to different analyzer angles. Therefore, the reflectance beam represented by one analyzer angle does not strike the same point on the CCD camera as the reflectance beam represented by another analyzer angle. This effect is known as beam walking. Since the intensities of the phase shifted beams must add vectorily on a common pixel for accurate readings, beam walking presents a serious deficiency in the precision of ellipsometric microscopes.

The microscopic imaging ellipsometer (MIE) developed by Beaglehole is a PCSA-type ellipsometric microscope. The Beaglehole microscope is similar to the DIM with the exception that it measures the coefficient of ellipticity, $\bar{\rho}$, at the Brewster angle, $\theta_B$ and the compensator rather than the analyzer is rotated to various angles where the reflected intensity is measured. Therefore the defocusing and beam walking problems associated with the DIM are present in the Beaglehole ellipsometric micro scope.

The Beaglehole microscope utilizes a white light source and a 600 nm filter to create the monochromatic incident light beam necessary to measure the coefficient of ellipticity. However, the CCD camera used in the Beaglehole microscope is not sensitive enough to be used with such a light source due to the weak signal of the light source. This leads to inaccuracies in the measurement of the film thickness.

The Hénon and Meunier microscope is a reflectometer with a PCSA-type configuration based upon the Beaglehole microscope, the only differences being the use of a high power, 0.5 W, Ar-ion laser as a light source, and the polarization of the incident beam in the p direction. However, as is inherent in ellipsometric microscopes which operate at the Brewster angle, a large amount of the energy of the incident beam is absorbed into the film sample. Therefore, by using the Ar-ion high powered laser, the Hénon and Meunier reflectometer may damage or otherwise physically alter the characteristics of the film sample being measured. The defocusing and beam walking problems associated with the other prior art ellipsometric microscopes are associated with the Hénon and Meunier microscope as well.

The Gaussian variance in the beam profile, where the intensity of the beam is greater at the center, tapering as a function of the radial distance from the center of the beam, causes inaccuracies in the measured intensity values of the reflectance beam. The prior art ellipsometric microscopes only provide an overall frame calibration, and not a pixel by pixel calibration, thereby reducing the lateral spatial resolution, and, thus, the utility of the CCD camera. Therefore, the prior art presents significant and heretofore unsolved needs to provide an ellipsometric microscope which can provide thin film thickness information as a continuous function of position, eliminate beam walking, and perform a pixel by pixel calibration for the intensities detected to overcome the Gaussian variation in the profile of the light beam.

SUMMARY OF THE INVENTION

The present invention solves the prior art problems discussed above and provides a distinct advance in the state of the art. More particularly, the ellipsometric microscope hereof includes the abilities of accurately determining the thickness of thin films as a function of position, eliminating beam walking associated with taking the necessary measurements to determine the coefficient of ellipticity, and providing a pixel by pixel calibration for the intensities detected to eliminate the Gaussian variances in the profile of the light beam.

The preferred ellipsometric microscope broadly includes light source means for emitting an incident beam of monochromatic, collimated light, means for directing the incident beam along an incident path for impingement on the film sample at a predetermined angle, there being a reflectance beam including a plurality of components, the reflectance beam reflecting from the film sample along a reflectance path, polarization means for elliptically polarizing the incident beam, means for altering the elliptical polarization of the incident beam, detecting means for detecting the reflectance beam, analyzing means coupled with the detecting means for analyzing the reflectance beam for determining the thickness of the film sample, and beam expansion means positioned in the reflectance path between the film sample and the detecting means for expanding the beam of light, and permitting only passage of parallel components of the reflectance beam. The microscope further includes means for altering the elliptical polarization of the incident beam without mechanical movement of the optical components, and calibration means for calibrating the intensity of the reflectance beam in a pixel by pixel fashion.

The light source means of the preferred embodiment is a laser light source. Other lights sources may also be used. For example, a Xenon light source having a monochrometer emits a beam of selectable monochromatic light which may be used to measure the thickness of the film sample. Such a Xenon light source has the ability to adjust the wavelength of the beam of light, which is desirable when measuring the thickness of the different film layers in a sample having a plurality of film layers.

The direction means includes a support assembly which includes an upright support beam, an incident arm pivotally coupled with a reflectance arm, and a worm screw. The worm screw is used to adjust the incidence angle of the incidence beam, and thus the reflectance angle of the reflectance beam. The incident arm and reflectance arms support the various optical components of the microscope.

The polarization means includes a polarizer and a variable retarder positioned along the incident beam path. These optical components elliptically polarize the incident beam, and may be electrically adjusted to alter the elliptical polarization in order to measure the thickness of the film sample.

The detection means is positioned so that the reflectance beam strikes the detection means, and includes a detector camera, such as a charged coupled detector (CCD) camera. The CCD camera includes an array of pixels which record the intensity of the reflectance beam.

The analyzing means includes a computer connected to the CCD camera, and a computer program installed in the computer which is designed to interpret the measured intensities of the reflected beam in order to quantify the intensities in terms of the coefficient of ellipticity, and, thus, determine the thickness of the film sample.

The beam expansion means ensures that only those components of the reflectance beam which are parallel upon entering the beam expansion means strike the CCD camera. The beam expansion means does not form a real image on the camera, as in the prior art, and, therefore, the prior art problem of defocusing resulting from the distorted image plane is solved.

The means for altering the elliptical polarization of the incident beam without mechanical movement of the optical components includes the use of a liquid crystal variable retarder along the incident beam path. Such a retarder is controlled by the computer, and allows the elliptical polarization of the incident beam to be altered by varying the voltage supplied to the retarder. Therefore, the prior art problem of beam walking is eliminated. A calibration means for calibrating the intensity of the reflectance beam eliminates spatial variation in the intensity of the reflectance beam. Therefore, film thickness may be calculated as a continuous function of position is also included to counteract the Gaussian intensity variance inherent in the reflectance beam.

DETAILED DESCRIPTION OF THE PREFERRED EMBODIMENTS

Figure 1:
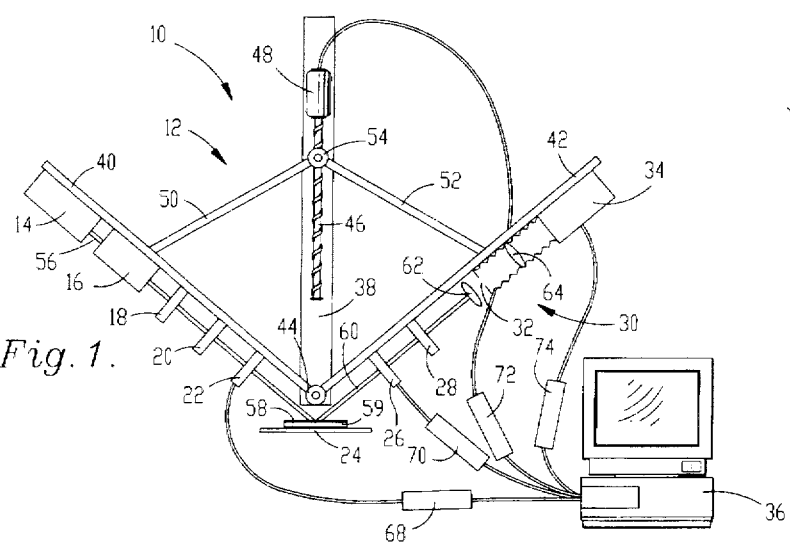
FIG. 1 is a schematic diagram of the preferred apparatus of the present invention.

FIG. 1 is a schematic diagram illustrating preferred apparatus 10 of the present invention. Apparatus 10 includes support assembly 12, light source 14, light intensity stabilizer 16, neutral density filter 18, linear polarizer 20, incident variable retarder 22, vibration isolation sample support 24, reflected variable retarder 26, reflected linear polarizer 28, beam expander 30, iris 32, charge coupled device (CCD) camera 34 having face 35, and computer 36.

Support assembly 12 includes upright support beam 38, incident arm 40 pivotally coupled with reflectance arm 42 by pivot 44 mounted adjacent the lower end of beam 38, worm screw 46 extending along the face of beam 38 and coupled with stepping motor 48, and extension rod 50 pivotally coupled with extension rod 52 by pivot 54. Worm screw 46 is threadably received by pivot 54 and the distal ends of rods 50, 52 are hingedly coupled with arms 40, 42. Incident arm 40 supports and aligns components 14, 16, 18, 20 and 22 and reflectance arm 42 supports and aligns components 26, 28, 30, 32 and 34.

Light source 14 is preferably a 5 mW He—Ne laser available from Melles Griot emitting a monochromatic beam of light having a wavelength of about 632.8 nm. Typically He—Ne lasers present intensity fluctuations of approximately 2%. Providing intensity stabilizer 16, available from Conoptic, Inc., reduces laser noise by a ratio of about 250/1 at 200 Hz. Neutral density filter 18 reduces the laser intensity from light source 14 to approximately between 1.0 and 2.0 µW. Light source 14 emits incident beam 56 which impinges upon thin film sample 58 covering structure 59 as reflected therefrom to present reflectance beam 60.

Figure 2:
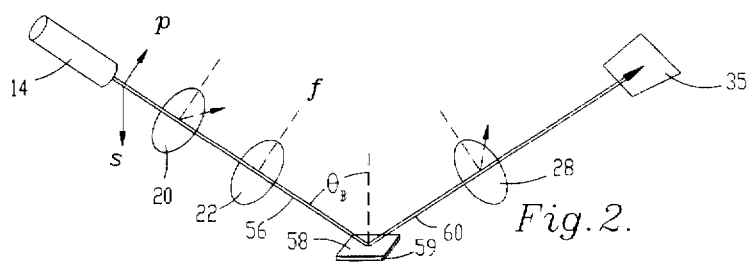
FIG. 2 is a diagrammatic representation of the beam paths and components of the apparatus of FIG. 1.

Linear polarizers 20 and 28 are sheet polarizers available from Meadowlark Optics and each presents an extinction ratio of $10^{-5}$. Polarizers 20, 28 are oriented at 45° to the s and p polarization directions, as depicted in FIG. 2, in order to pass equal amplitudes of both polarizations. Thus, the electric vector of the light after polarizer 20 is $$\vec{E}_1 = \frac{E_o}{\sqrt{2}} (\hat{p} + \hat{s}),$$

where $E_o$ is the initial amplitude and $\hat{p}$ is the unit vector for the p polarization direction, and $\hat{s}$ is the unit vector for the s polarization direction.

Figure 3:
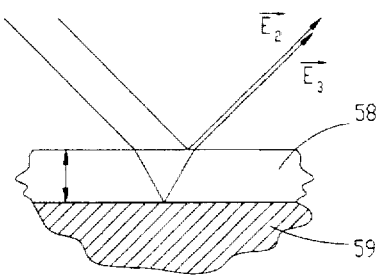
FIG. 3 is a reflection diagram of the interaction of the light beam of the apparatus of FIG. 1 interacting with a film sample.

Retarders 22 and 26 are liquid crystal variable retarder plates available from Meadowlark Optics and controlled by computer 36 as explained further below. For retarder 22, the optical axis of the plate is set parallel to the p direction. FIG. 2 depicts retarder 22 having optical axis f. The electric field of incident beam 56 after passing through the retarder 22 is $$\vec{E}_2 = \frac{E_o}{\sqrt{2}} (e^{-i\delta}\hat{p} + \hat{s}),$$

where $-\delta$ represents the phase shift of incident beam 56 upon passage through the retarder 22. After reflecting from the surface of film sample 58, the electric field of reflectance beam 60 is $$\vec{E}_3 = \frac{E_o}{\sqrt{2}} (\rho_p e^{i(\delta_p - \delta)}\hat{p} + \rho_s e^{i\delta_s}\hat{s}),$$

where $\rho_p$ and $\delta_p$ represent the reflection amplitude and phase shift in the p direction, respectively, $\rho_s$ and $\delta_s$ represent the reflection amplitude and phase shift in the s direction, respectively, due to reflectance from film sample 58 and structure 59. FIG. 3 depicts the reflectance of incident beam 56 from film sample 58 and structure 59.

Reflectance beam 60 then passes through retarder 26, which is oriented parallel to the p direction, and linear polarizer 28, which is set at 45° to the p and s directions. After polarizer 28, the electric field is $$\vec{E}_4 = \frac{E_o}{2} (\rho_p e^{i(\delta_p - \delta)} + \rho_s e^{i\delta_s})\hat{P},$$

where $\hat{P}$ is polarization unit vector for the direction at 45° to p and s polarization directions. The light intensity on camera 34 is $$I = \vec{E}_4 \cdot \vec{E}_4^* = \frac{E_o^2}{4} \rho_s^2 (1 + \rho^2 + 2\rho\cos[\Delta - \delta]),$$

where $\Delta \equiv \delta_p - \delta_s$ and $\rho \equiv |r_p/r_s| = \rho_p/\rho_s$.

Beam expander 30 is composed of a microscope object lens 62 and a convex lens 64 to provide a magnification ratio of about 9.77. A shear plate, available from Melles Griot, is used to correctly position lenses 62 and 64 to ensure that parallel light incident on lens 62 is magnified and exits lens 64 as parallel light. The shear plate is not used in the normal operation of the ellipsometric microscope once the lenses 62 and 64 have been correctly positioned. Iris 32 is located at the confocal point of lenses 62, 64 and allows only the reflected laser light, that is, reflectance beam 60, to strike CCD camera 34.

CCD camera 34 is a thermoelectrically cooled, slow scan, CCD camera available from Princeton Instruments, Inc. and presents a full well capacity per pixel of about 500,000 photoelectrons. The quantum efficiency of camera 34 is about 40% and it has 512×512 pixels with a 16 bit resolution for each pixel of size 27×27 µm². Each pixel images an area of about 3×11 µm² on the film sample surface for which the intensity can be determined to better than one part in 65,000. The shutter opening time for camera 34 is typically set at 50 ms.

Computer 36 is preferably a Macintosh Centris 650 personal computer with 40 Mbyte of memory. Computer 36 is electrically coupled with and controls retarders 22, 26 and stepping motor 48 and receives the output from camera 34.

Computer 36 is connected to retarder 22 via retarder controller 68. Retarder controller 68 is preferably a liquid crystal digital interface controller available from Meadowlark Optics, Model #ILV-D1040. Computer 36 includes a GPIB interface card available from National Instruments for operating controller 68.

Retarder controller 70 is a liquid crystal controller Model #CLV-B1020 available from Meadowlark Optics. Computer 36 includes a 24-bit parallel digital I/O interface card available from National Instruments for operating controller 70, and, thus, adjusting retarder 26.

Computer 36 is connected to stepping motor 48 via stepping motor controller 72. Controller 72, is available from Biomedical Technology, Inc., Model #SMC-212A. The GPIB interface card is connected to controller 72 for operation of stepping motor 48.

Computer 36 is connected to CCD camera 34 via detector controller 74. Controller 74 is preferably Model #ST-135, available from Princeton Instruments. The GPIB interface card is connected to controller 74 for operating camera 34 and collecting intensity data from reflectance beam 60.

Computer 36 controls the operation of apparatus 10 according to the computer program shown in Appendix I. The preferred program is written in National Instruments LabView 3.0.1. In general, apparatus 10 measures the thickness of film sample 58 by measuring the intensities, $I_{\pi/2}$ and $I_{3\pi/2}$, intensity of reflectance beam 60 at two different phase angles, $\delta=\pi/2$ and $\delta=3\pi/2$, as selected by incident retarder 22. From these intensity measurements, a ratio is determined in computer 36. This ratio is the coefficient of ellipticity, $\bar{\rho}$, which can be directly interpreted in terms of a thickness variation according to the so-called Drude equation $$\bar{\rho} = Im\left(\frac{r_p}{r_s}\right)\bigg|_{\theta_B} = \frac{\pi}{\lambda} \frac{\sqrt{\epsilon_1 + \epsilon_2}}{\epsilon_1 - \epsilon_2} \int \frac{[\epsilon(z) - \epsilon_1][\epsilon(z) - \epsilon_2]}{\epsilon(z)} dz$$

which is valid for thin films having a thickness that is much less than the wavelength of light, and where the incident angle is equal to the Brewster angle. In the Drude equation, $\epsilon(z)$ represents the dielectric profile as a function of depth z perpendicular to the surface of film sample 58. The dielectric profile varies from $\epsilon_1$, the vapor dielectric constant, to $\epsilon_2$, the bulk substrate dielectric constant.

Apparatus 10 of the present invention has a thickness resolution of about 1 Å with lateral spatial resolution of about 1 µm. In operation, arms 40 and 42 are initially adjusted so that incident beam 56 is directed at film sample 58 at the so-called Brewster angle, $\theta_B$, as represented in FIG. 2. The Brewster angle is that angle where the real component of the complex reflection amplitudes, $Re(r_p/r_s)$, vanishes, and the imaginary component, $Im(r_p/r_s)$, becomes the coefficient of ellipticity, $\bar{\rho}$. The real component, $Re(r_p/r_s)$, is determined by using the following equation $$\frac{I_0 - I_\pi}{I_0 - I_\pi} = \frac{2\rho\cos\Delta}{1 + \rho^2} \approx 2\rho\cos\Delta = 2Re\left(\frac{r_p}{r_s}\right),$$

where $I_0$ represents the reflected intensity of beam 60 on camera 34 where the phase shift of retarder 22, $\delta$, is 0, and $I_\pi$, represents the reflected intensity of beam 60 for $\delta=\pi$. A measurement of $Re(r_p/r_s)$ is initially made for the phase shift of retarder 26 set to 0 which corresponds to the unit vector $\hat{P}$ of polarizer 28 at +45° to the p direction. An additional measurement of $Re(r_p/r_s)$ is made for the phase shift of retarder 26 set to π, which correspond to $\hat{P}$ of linear polarizer 28 at –45° to the p direction. Under such circumstances, only the sign of the right hand side of equation 7 is changed. An average value for $Re(r_p/r_s)$ is determined by taking the difference between these two readings. Computer 36 controls stepping motor 48 to adjust the arms 40 and 42 until $Re(r_p/r_s)$ vanishes.

Once the Brewster angle is set, apparatus 10 is now ready to measure the thickness of film sample 58 by determining the imaginary component of the complex reflection amplitude, $Im(r_p/r_s)$. This imaginary component is determined using the measured intensities $I_{\pi/2}$ and $I_{3\pi/2}$, where the phase shift of retarder 22 is set respectively to $\delta=\pi/2$ and $\delta=3\pi/2$, and is represented by the following equation $$\frac{I_{\pi/2} - I_{3\pi/2}}{I_{\pi/2} + I_{3\pi/2}} = \frac{2\rho\sin\Delta}{1 + \rho^2} \approx 2\rho\sin\Delta = 2Im\left(\frac{r_p}{r_s}\right).$$

A measurement of the imaginary component is initially made for the chase shift of retarder 26 set to zero. An additional measurement of the imaginary component is made for the phase shift of retarder 26 set to π. Under such circumstances, only the sign of the right hand side of the equation above is changed. An average value for the imaginary component is determined by taking the difference of these two readings. For thin films, the value for $\rho^2$ in the denominator of the equation above is negligible compared with one, and the imaginary component can be determined directly from $Im(r_p/r_s)$. For uniform thin films, $\epsilon(z)$ is a constant independent of z and the film thickness can be determined from $Im(r_p/r_s)$ and the Drude equation.

In determining the average values for the real and imaginary components of the complex reflection amplitudes, the polarization vector, P, of polarizer 28 is shifted between ±45° in order to remove any systematic errors caused by birefringence effects inherent in the optical components 20, 22, 26, 28 and 30. This procedure is known as the zone averaging method.

By calculating the ratio of the difference and sum between the reflected intensities of beam 60 for phase angles $\delta=\pi/2$ and $\delta=3\pi/2$ described above, the effects of Gaussian variance in the profile of beam 60 are eliminated. Those skilled in the art will appreciate that by determining the intensity ratio above, the term $E_0$ drops out of the ratio equation. Thus, any variance effects of $E_0$, due to the Gaussian nature of light, and, therefore, variances in the intensity of reflectance beam 60, have no effect on the ratio equation, and, thus, a pixel by pixel calibration is achieved which eliminates any spatial variation in the intensity of reflectance beam 60, and, therefore, provides thickness information as a continuous function of position.

Beam expander 30 having iris 32 and lenses 62, 64, ensures that only those components of beam 60 which are parallel with respect to each other strike camera 34. This scheme relies upon the collimated coherence properties of laser light, much as in interferometry, and, therefore, the need to form a real image on camera 34, as in the prior art, is not necessary. Since no real image is formed on camera 34, there is no inclined image plane distortion. An accurate image of film sample 58 impinged upon by incident beam 56 is then formed. As a result, there is no need to scan the surface of film sample 58, and the prior art problem of defocusing caused by an inclined image plane is solved.

The prior art problem of beam translation, also known as beam walking, is caused by the rotation of various optical elements. Apparatus 10 eliminates beam walking by utilizing variable retarders 22 and 26. It will be appreciated by those skilled in the art, that variable retarder 22 controlled by computer 36 and controller 68 allows shifting of the phase angles, δ associated with incident beam 56 to be accomplished without mechanical movement thereof. The prior art problem of beam walking associated with phase angle shifting is thus solved.

Retarder 26 is used to shift the polarization angle between ±45° relative to the p direction in order to conduct the zone averaging method in order to negate any of the inherent birefringence effects in optical components. By using retarder 26 controlled by computer 36 and controller 70, the polarization angle may be shifted without mechanical movement thereof. As a result, the prior art problem of beam walking is solved by conducting the zone averaging method.

Although apparatus 10 has been described with reference to the illustrated embodiment, it is noted that variations and changes may be made and equivalents employed without departing from the scope of the invention recited in the claims. Light source 14, for instance, does not necessarily have to be a laser light source. It is possible to use a collimated light source, such as a Xenon light source, having variable wavelengths available for the emitted light beam. A monochrometer permitting passage of one distinct wavelength would be necessarily included for accurate measurements. Monochrometers are generally adjustable so that the wavelength of incident beam 56 would then also be adjustable. The availability of a plurality of incident beam wavelengths is desirable when film sample 58 includes a plurality of distinct film layers. Additionally, such a light source would allow determination of the dielectric constant ε of the film, and a thickness determination of the film sample not only for thin films but also for thick films which have a thickness that is in the range of, or greater than the wavelength of light by measuring the real and imaginary components at various incident angles and differing wavelengths. The Drude equation is not used for thick film measurement.

Incident beam 56 may be delivered to incident arm 40 via a fiber optic cable provided that the output connector of the fiber optic cable is rigidly mounted to arm 40 and the incident beam 56 is accurately collimated. If a polarized laser is used as the light source then it may be advantageous to use a single-mode polarization preserving fiber optic cable.

A Pockels cell, Kerr cell, or other appropriate voltage controlled device, may be used in place of retarders 22, 26. The Pockels cell and Kerr cell are voltage controlled devices which may be used to shift the phase angle of incident beam 56. Such devices offer faster switching times than retarders 22, 26, and may be preferable where film sample 58 is on top of a liquid substrate. Vibration isolation is more difficult when film sample 58 is covering a liquid, thereby making the faster switching times associated with the Pockels cell and Kerr cell more desirous in such applications.

The area of film sample 58 upon which incident beam 56 impinges may be enlarged through the use of a beam expander provided on incident arm 40 in the path of incident beam 56. A beam expander in such a position would allow thickness to be determined for a larger portion of film sample 58. A beam expander provided on incident arm 40 would have the adverse effect of reducing the lateral spatial resolution.

A zoom beam expander may be used in place of beam expander 30. Such a device would allow the operator of apparatus 10 to view a large area of film sample 58, and zoom in on an isolated area of interest. Areas of interest generally reside where a deformity in film sample 58 is detected. The zoom beam expander and camera 34 may be mounted on an X-Y translation stage in order to shift the region of interest into view.

What is claimed is:

1. An apparatus for measuring the thickness of a thin film sample, the apparatus comprising:

light source means for emitting an incident beam of monochromatic, collimated light;

means for directing said incident beam along an incident path for impingement on the film sample at a predetermined, non-normal angle with respect thereto, there being a reflectance beam reflecting from the film sample along a reflectance path, said reflectance beam including a plurality of components, said components presenting phase angles;

polarization means for elliptically polarizing said incident beam, said polarizing means including means for shifting said phase angles of said components;

detecting means including a charged coupled device camera having a detection face for detecting said reflectance beam;

analyzing means coupled with said detecting means for analyzing said reflectance beam for determining the thickness of the film sample; and beam expansion means positioned in said reflectance path between the film sample and said detecting means for expanding said reflectance beam, and permitting passage of said components of said reflectance beam to said detection face that are generally parallel with respect to each other without forming a real image of the sample on said detection face of said detecting means.

2. The apparatus as set forth in claim 1, wherein said beam expansion means includes an object lens, a convex lens, and an iris positioned along said reflectance path, said object and convex lenses defining a confocal point, said iris being positioned at said confocal point.

3. The apparatus as set forth in claim 2, wherein said light source means includes a laser light source.

4. The apparatus as set forth in claim 3, wherein said laser light source is a helium-neon laser.

5. The apparatus as set forth in claim 2, wherein said polarization means includes a liquid crystal variable retarder positioned along said incident path.

6. The apparatus as set forth in claim 1, wherein said charged coupled device camera includes an array of 512× 512 pixels.

7. The apparatus as set forth in claim 1, wherein said incident beam includes components presenting phase angles, and said polarization means includes means for selectively changing said phase angles without mechanical movement.

8. The apparatus as set forth in claim 7, said wherein means for selectively changing said phase angles includes a liquid crystal variable retarder positioned along said incident path.

9. The apparatus as set forth in claim 8, further including a liquid crystal variable retarder positioned along said reflectance path.

10. The apparatus as set forth in claim 7, wherein said means for selectively changing said phase angles includes a pockels cell positioned along said incident path.

11. The apparatus as set forth in claim 7, wherein said means for selectively changing said phase angles includes a kerr cell positioned along said incident path.

12. The apparatus as set forth in claim 1, wherein said charged coupled device camera includes an array of 512× 512 pixels.

13. An apparatus for measuring the thickness of a thin film sample, the apparatus comprising:

light source means for emitting an incident beam of monochromatic, collimated light;

means for directing said incident beam along an incident path for impingement on the film sample at a predetermined, non-normal angle with respect thereto, there being a reflectance beam reflecting from the film sample along a reflectance path, said reflectance beam including a plurality of components;

polarization means for elliptically polarizing said incident beam, and for altering the elliptical polarization of said incident beam;

detecting means including a charged coupled device camera having a detection face for detecting said reflectance beam;

analyzing means coupled with said detecting means for analyzing said reflectance beam for determining the thickness of the film sample; and beam expansion means positioned in said reflectance path between the film sample and said detecting means for expanding said reflectance beam, and for preventing passage of said components of said reflectance beam to said detection means that are generally not parallel with respect to each other, said beam expansion means permitting passage of generally parallel components of said reflectance beam to said detection means without forming a real image of the sample on said detection face of said detecting means.

* * * * *